US008853247B2

(12) United States Patent
Ren et al.

(10) Patent No.: US 8,853,247 B2
(45) Date of Patent: Oct. 7, 2014

(54) OLIGOMER-NITROIMIDAZOLE ANTI-INFECTIVE CONJUGATES

(75) Inventors: Zhongxu Ren, Madison, AL (US); Jennifer Riggs-Sauthier, Huntsville, AL (US); Michael D. Bentley, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 255 days.

(21) Appl. No.: 12/739,605

(22) PCT Filed: Oct. 31, 2008

(86) PCT No.: PCT/US2008/012416
§ 371 (c)(1),
(2), (4) Date: Aug. 25, 2010

(87) PCT Pub. No.: WO2009/058387
PCT Pub. Date: May 7, 2009

(65) Prior Publication Data
US 2010/0317707 A1 Dec. 16, 2010

Related U.S. Application Data

(60) Provisional application No. 61/001,655, filed on Nov. 2, 2007.

(51) Int. Cl.
*A61K 31/41* (2006.01)
*A61K 47/48* (2006.01)

(52) U.S. Cl.
CPC ............................. *A61K 47/48215* (2013.01)
USPC .................................. 514/359; 514/772.3

(58) Field of Classification Search
USPC ............................................. 514/359, 772.3
See application file for complete search history.

(56) References Cited

U.S. PATENT DOCUMENTS

| 2,944,061 | A | 7/1960 | Jacob et al. |
| 5,672,662 | A | 9/1997 | Harris et al. |
| 2005/0080260 | A1 | 4/2005 | Mills et al. |
| 2005/0136031 | A1 | 6/2005 | Bentley et al. |

FOREIGN PATENT DOCUMENTS

| WO | WO 91/18630 | 12/1991 |
| WO | WO 02/098949 | 12/2002 |
| WO | WO 2006/130799 | 12/2006 |

OTHER PUBLICATIONS

Bersani, et al., "PEG-metronidazole conjugates: synthesis, in vitro and in vivo properties.," IL Farmaco, vol. 60, No. 9, pp. 783-788, (2005).
Chen, et al., "Synthesis and Properties of ABA Amphiphiles," J. Org. Chem., vol. 64, pp. 6870-6873, (1999).
Cho, et al., "Metronidazole Phosphate—A Water-Soluble Prodrug for Parenteral" J. of Pharm. Sci., vol. 71 No. 4, pp. 410-414, (Apr. 1982)
Holley, et al., "Uptake and Cytotoxicity of and Cytotoxicity of Novel Nitroimidazole-Polyamine Conjugates in Ehrlich Ascites Tumour Cells," Biochem. Phamacol., vol. 43, No. 4, pp. 763-769, (1992).
Larsen, et al., "Macromolecular prodrugs IV. Kinetics of hydrolysis of metronidazole monosuccinate dextran ester conjugates in aqueous solution and in plasma-sequential release of metronidazole from the conjugates at physiological pH.," Intl. J. of Pharmaceu., vol. 35, pp. 39-45, (1987).
Larsen, et al., "Macromolecular prodrugs IX. ," Acta Phamnaceu. Suecica, vol. 25, No. 1, pp, 1-14, (1988).
Parrick, et al., "Targeting Radiosensitizers to DNA by Minor Groove Binding: Nitroarenese Based on Netropsin and Distamycin," Bioorg. & Med. Chem. Lett., vol. 3, No. 8, pp. 1697-1702, (1993).
Upcroft, et al., "5-Nitromidazole Drugs Effective against Metronidazole-Resistant *Trichomonas vaginalis* and *Giardia duodenalis*," Antimicrob. Agents and Chemother., vol. 50, No. 1, pp. 344-347, (Jan. 2006).
Upcroft, et al., "Efficacy of New 5-Nitroimidazoles against Metronidazole-Susceptible and -Resistant Giardia, *Trichomonas*, and *Entabmoeba* spp.," Antimicrob, Agents and Chemother., vol. 43. No. 1, pp. 73-76, (Jan. 1999).
Walsh, et al., "Solid Phase Synthesis of a Metronidazole Oligonucleotide Conjugate," Molecules, vol. 11, pp. 486-495, (2006).
PCT International Search Report corresponding to PCT Application No. PCT/US2008/012416 date of mailing Oct. 7, 2009.
PCT International Preliminary Report On Patentability corresponding to PCT Application No. PCT/US2008/012416 date of mailing May 14, 2010.
Enzon Pharmaceuticals, Macromolecular Engineering Technologies, pp. 1-14, (2004).
Nektar198 —Transforming Therapeutics, Nektar Molecule Engineering: Polyethylene Glycol and Derivatives for Advanced PEGylation, pp. 1-20, Catalog—2003, (Jul. 2003).
Nektar™—Transforming Therapeutics, Nektar Advanced PEGylation: Polyethylene Glycol and Derivatives for Advanced PEGylation, pp. 1-24, Catalog—2004, (Jul. 2004).
Nektar™—Transforming Therapeutics, Nektar Advanced PEGylation: Polyethylene Glycol and Derivatives for Advanced PEGylation, pp. 1-30, (Catalog 2005-2006).
NOF Corporation, "PEG Derivatives, Phospholipid abd Drug Delivery Materials for Pharmaceuticals", pp. 1-46, Catalogue 2003-1st, (Jan. 2003).
NOF Corporation, "PEG Derivatives, Phospholipid and Drug Delivery Materials for Pharmaceuticals", pp. 1-50, Catalogue 2003-2nd, (Mar. 2004).
NOF Corporation, "PEG Derivatives, Phospholipids and Drug Delivery Materials for Pharmaceutical Products and Formulations", pp. 1-59, Catalogue Ver. 8, (Apr. 2006).
Polypure, Products; PEG amines; PEG acids and amino acids; PEG thiols and disulfides; BIOTINS, (Apr. 2004).
Polypure, Products; PEG amines; PEG acids and amino acids; PEG thiols and disulfides; BIOTINS, (Apr. 2005).

(Continued)

*Primary Examiner* — Renee Claytor
*Assistant Examiner* — Shobha Kantamneni
(74) *Attorney, Agent, or Firm* — Mark A. Wilson

(57) ABSTRACT

The invention provides (among other things) small molecule drugs that are chemically modified by covalent attachment of a water soluble oligomer.

5 Claims, No Drawings

(56) References Cited

OTHER PUBLICATIONS

Quanta Biodesign, Labeling, Derivatization and Crosslinking Reagents for Biological and Related Materials with dPEG™, pp. 1-38, (Mar. 12, 2004).

Quanta Biodesign, Labeling, Modification and Crosslinking Reagents incorporating our unique monodispersed dPEG™ Technology, pp. 1-31, (Nov. 5, 2004).

Quanta Biodesign, Ltd., Leading innovator, producer and provider of monodisperse discrete PEG™ (dPEG™) derivatives, (Product Catalog), pp. 1-51, (Updated: Jul. 18, 2005).

Quanta Biodesign, Ltd., Leading innovator, producer and provider of monodisperse discrete PEG™ (dPEG™) derivatives, (Product Catalog), pp. 1-51, (Updated: Nov. 17, 2005).

Shearwater Polymers, Inc., Polyethylene Glycol and Derivatives, pp. 1-49, (Catalog—Mar. 1995).

Shearwater Polymers, Inc., Polyethylene Glycol and Derivatives, pp. 1-53, (Catalog—Jul. 1997).

Shearwater Polymers, Inc., Polyethylene Glycol and Derivatives: Functionalized Biocompatible Polymers for Research and Pharmaceuticals, pp. 1-50, (Catalog—Jan. 2000).

Shearwater Corporation, Polyethylene Glycol and Derivatives for Biomedical Applications, pp. 1-17, (Catalog—Jul. 2001).

Amidon, et al., "Absorption of Peptide and Peptidomimetic Drugs", Annu. Rev. Pharmacol. Toxicol., vol. 34, pp. 321-341, (1994).

Freeman, et al., "Metronidazole: A Therapeutic Review and Update", Drugs, vol. 54, No. 5, pp. 679-708, (1997).

He, et al., "Species Differences in Size Discrimination in the Paracellular Pathway Reflected by Oral Bioavailability of Poly(ethylene glycol) and $_D$-Peptides", Journal of Pharmaceutical Sciences, vol. 87, No. 5, (May 1998).

Soderholm, et al., "Absorption Profiles for Polyethylene Glycols After Regional Jejunal Perfusion and Oral Load in Healthy Humans", Digestive Diseases and Sciences, vol. 42, No. 4, pp. 853-857, (Apr. 1997).

Yamaoka, et al., "Distribution and Tissue Uptake of Poly(ethylene glycol) with Different Molecular Weights after Intravenous Administration to Mice", Journal of Pharmaceutical Sciences, vol. 83, No. 4, (Apr. 1994).

OLIGOMER-NITROIMIDAZOLE ANTI-INFECTIVE CONJUGATES

CROSS REFERENCE TO RELATED APPLICATIONS

This application is a 35 U.S.C. §371 application of International Application No. PCT/US2008/012416, filed Oct. 31, 2008, designating the United States, which claims the benefit of priority under 35 U.S.C. §119(e) to U.S. Provisional Patent Application No. 61/001,655, filed Nov. 2, 2007, both of which are hereby incorporated by reference in their entireties.

FIELD OF THE INVENTION

This invention comprises (among other things) chemically modified nitroimidazole anti-infectives that possess certain advantages over nitroimidazole anti-infectives lacking the chemical modification. The chemically modified nitroimidazole anti-infectives described herein relate to and/or have application(s) in (among others) the fields of drug discovery, pharmacotherapy, physiology, organic chemistry and polymer chemistry.

BACKGROUND OF THE INVENTION

Nitroimidazole anti-infectives represent a class of agents employed in the treatment of individuals suffering from a variety of infections. Metronidazole, a member of the nitroimidazole anti-infectives class, has been used in the treatment of individuals suffering from anaerobic infections, intra-abdominal infections, skin and skin structure infections, gynecologic infections, bacterial septicemia, bone and joint infections, CNS infections, respiratory tract infections, endocarditis caused by *Bacteroides* species, amebiasis, trichomoniasis, bacterial vaginosis, acne rosacea, hepatic encephalopathy, Crohn's disease, diarrhea associated with *Clostridium difficile, Heliobacter pylori* infections, recurrent urethritis, and pelvic inflammatory disease.

With respect to Crohn's disease, for example, metronidazole is active against anaerobic bowel flora and has been used for prophylaxis and treatment of patients suffering from this disease. Although a cause and effect relationship has not been established, Crohn's disease patients who have been treated with metronidazole at high doses for extended periods of time have been known to have an increased incidence of certain extraintestinal cancers, such as breast cancer. In view of the general desire to limit the exposure of xenobiotics only to affected tissues generally, and in view of the potential for extraintestinal side effects caused by metronidazole-based pharmacotherapy in the treatment of patients suffering from Crohn's disease in particular, it would be desirable to have a drug that has decreased exposure extra-intestinally while possessing nitroimidazole anti-infective activities and/or have other advantages.

The present invention seeks to address these and other needs in the art.

SUMMARY OF THE INVENTION

In one or more embodiments of the invention, a compound is provided, the compound comprising a nitroimidazole anti-infective residue covalently attached via a stable or degradable linkage to a water-soluble, non-peptidic oligomer.

Exemplary compounds of the invention include those having the following structure:

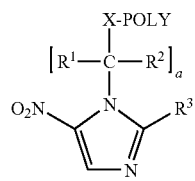

(Formula I-C)

wherein:
(a) is 2, 3, or 4;
each instance of $R^1$ is independently selected from the group consisting of hydrogen and alkyl (preferably hydrogen);
each instance of $R^2$ is independently selected from the group consisting of hydrogen and alkyl (preferably hydrogen);
$R^3$ is selected from the group consisting of hydrogen and alkyl (preferably $C_{1-5}$ alkyl);
X is a spacer moiety; and
POLY is a water-soluble, non-peptidic oligomer.

The "nitroimidazole anti-infective residue" is a compound having a structure of a nitroimidazole anti-infective that is altered by the presence of one or more bonds, which bond(s) serve as the means to link (either directly or indirectly) one or more water-soluble, non-peptidic oligomers. Exemplary nitroimidazole anti-infectives have a structure encompassed by Formula I:

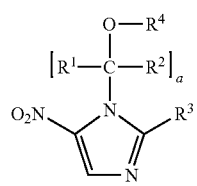

(Formula I)

wherein:
(a) is 2, 3, or 4;
each instance of $R^1$ is independently selected from the group consisting of hydrogen and alkyl (preferably hydrogen);
each instance of $R^2$ is independently selected from the group consisting of hydrogen and alkyl (preferably hydrogen);
$R^3$ is selected from the group consisting of hydrogen and alkyl (preferably $C_{1-5}$ alkyl); and
$R^4$ is selected from the group consisting of hydrogen, alkyl, acyl residue of a monocarboxylic aliphatic acid, acyl residue of a dicarboxylic aliphatic acid, acyl residue of a monocarboxylic aromatic acid and acyl residue of a dicarboxylic aromatic acid.

In one or more embodiments of the invention, a composition is provided, the composition comprising a compound comprising a nitroimidazole anti-infective residue covalently attached via a stable or degradable linkage to a water-soluble and non-peptidic oligomer, and optionally, a pharmaceutically acceptable excipient.

In one or more embodiments of the invention, a dosage form is provided, the dosage form comprising a compound comprising a nitroimidazole anti-infective residue covalently attached via a stable or degradable linkage to a water-soluble, non-peptidic oligomer, wherein the compound is present in a dosage form.

In one or more embodiments of the invention, a method is provided, the method comprising covalently attaching a water-soluble, non-peptidic oligomer to a nitroimidazole anti-infective.

In one or more embodiments of the invention, a method is provided, the method comprising administering a compound comprising a nitroimidazole anti-infective residue covalently attached via a stable or degradable linkage to a water-soluble, non-peptidic oligomer.

These and other objects, aspects, embodiments and features of the invention will become more fully apparent to one of ordinary skill in the art when read in conjunction with the following detailed description.

DETAILED DESCRIPTION OF THE INVENTION

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic oligomer" indicates an oligomer that is at least 35% (by weight) soluble, preferably greater than 70% (by weight), and more preferably greater than 95% (by weight) soluble, in water at room temperature. Typically, an unfiltered aqueous preparation of a "water-soluble" oligomer transmits at least 75%, more preferably at least 95%, of the amount of light transmitted by the same solution after filtering. It is most preferred, however, that the water-soluble oligomer is at least 95% (by weight) soluble in water or completely soluble in water. With respect to being "non-peptidic," an oligomer is non-peptidic when it has less than 35% (by weight) of amino acid residues.

The terms "monomer," "monomeric subunit" and "monomeric unit" are used interchangeably herein and refer to one of the basic structural units of a polymer or oligomer. In the case of a homo-oligomer, a single repeating structural unit forms the oligomer. In the case of a co-oligomer, two or more structural units are repeated—either in a pattern or randomly—to form the oligomer. Preferred oligomers used in connection with present the invention are homo-oligomers. The water-soluble, non-peptidic oligomer typically comprises one or more monomers serially attached to form a chain of monomers. The oligomer can be formed from a single monomer type (i.e., is homo-oligomeric) or two or three monomer types (i.e., is co-oligomeric).

An "oligomer" is a molecule possessing from about 1 to about 125 monomers, preferably from about 2 to about 30 monomers. The architecture of an oligomer can vary. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" or oligoethylene glycol is one in which substantially all (preferably all) monomeric subunits are ethylene oxide subunits, though the oligomer may contain distinct end capping moieties or functional groups, e.g., for conjugation. PEG oligomers for use in the present invention will comprise one of the two following structures: "—(CH$_2$CH$_2$O)$_n$—" or "—(CH$_2$CH$_2$O)$_{n-1}$CH$_2$CH$_2$—," depending upon whether or not the terminal oxygen(s) has been displaced, e.g., during a synthetic transformation. As stated above, for the PEG oligomers, the variable (n) ranges from about 1 to 50 and the terminal groups and architecture of the overall PEG can vary. When PEG further comprises a functional group, A, for linking to, e.g., a small molecule drug, the functional group when covalently attached to a PEG oligomer does not result in formation of (i) an oxygen-oxygen bond (—O—O—, a peroxide linkage), or (ii) a nitrogen-oxygen bond (N—O, O—N).

The terms "end-capped" or "terminally capped" are interchangeably used herein to refer to a terminal or endpoint of a polymer having an end-capping moiety. Typically, although not necessarily, the end-capping moiety comprises a hydroxy or C$_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled, can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like.

"Branched," in reference to the geometry or overall structure of an oligomer, refers to an oligomer having two or more polymer "arms" extending from a branch point.

"Forked," in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, thiolesters, and carbonates.

An "enzymatically degradable linkage" means a linkage that is subject to degradation by one or more enzymes.

A "stable" linkage or bond refers to a chemical bond that is substantially stable in water, that is to say, does not undergo hydrolysis under ordinary physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Monodisperse" refers to an oligomer composition wherein substantially all of the oligomers in the composition have a well-defined, single molecular weight and defined number of monomers, as determined by chromatography or mass spectrometry. Monodisperse oligomer compositions are in one sense pure, that is, substantially having a single and definable number (as a whole number) of monomers rather than a large distribution. A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a large distribution and would possess a MW/Mn value of 1.0005, and more preferably, a MW/Mn value of 1.0000 if the oligomer were not attached to the moiety derived from a nitroimidazole anti-infective. A composition comprised of monodisperse conjugates may, however, include one or more nonconjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a large distribution, and whose distribution of molecular weights, when plotted as a number fraction versus molecular weight, appears as two separate identifiable peaks. Preferably, for a bimodal oligomer composition as described herein, each peak is generally symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and most preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1.0005 or less, and most preferably a MW/Mn value of 1.0000 if the oligomer were not attached to the moiety derived from a nitroimidazole anti-infective. A composition comprised of bimodal conjugates can include, however, one or more nonconjugate substances such as solvents, reagents, excipients, and so forth A "nitroimidazole anti-infective" refers to an organic, inorganic, or organometallic compound having a molecular weight of less than about 1000 Daltons and having some degree of activity as an anti-infective agent against one or more microorganisms.

"Alkyl" refers to a hydrocarbon chain ranging from about 1 to 20 atoms in length. Such hydrocarbon chains are preferably but not necessarily saturated and may be branched or straight chain. Exemplary alkyl groups include methyl, ethyl, propyl, butyl, pentyl, 2-methylbutyl, 2-ethylpropyl, 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, i-butyl, t-butyl.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, benzyl, etc.), preferably $C_1$-$C_7$.

"Pharmaceutically acceptable excipient" or "pharmaceutically acceptable carrier" refers to component that may be included in the compositions of the invention and causes no significant adverse toxicological effects to a patient.

The term "aryl" means an aromatic group having up to 14 carbon atoms. Aryl groups include phenyl, naphthyl, biphenyl, phenanthrenyl, naphthacenyl, and the like. "Substituted phenyl" and "substituted aryl" denote a phenyl group and aryl group, respectively, substituted with one, two, three, four or five (e.g. 1-2, 1-3 or 1-4 substituents) chosen from halo (F, Cl, Br, I), hydroxy, hydroxy, cyano, nitro, alkyl (e.g., $C_{1-6}$ alkyl), alkoxy (e.g., $C_{1-6}$ alkoxy), benzyloxy, carboxy, aryl, and so forth.

"Pharmacologically effective amount," "physiologically effective amount," and "therapeutically effective amount" are used interchangeably herein to mean the amount of a water-soluble oligomer-small molecule drug conjugate present in a composition that is needed to provide a desired level of active agent and/or conjugate in the bloodstream or in the target tissue. The precise amount may depend upon numerous factors, e.g., the particular active agent, the components and physical characteristics of the composition, intended patient population, patient considerations, and may readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterobifunctional.

A basic reactant or an acidic reactant described herein include neutral, charged, and any corresponding salt forms thereof.

The term "patient," refers to a living organism suffering from or prone to a condition that can be prevented or treated by administration of a conjugate as described herein, and includes both humans and animals.

"Optional" or "optionally" means that the subsequently described circumstance may but need not necessarily occur, so that the description includes instances where the circumstance occurs and instances where it does not.

As indicated above, the present invention is directed to (among other things) a compound comprising a nitroimidazole anti-infective residue covalently attached via a stable or degradable linkage to a water-soluble, non-peptidic oligomer.

In one or more embodiments of the invention, a compound is provided, the compound comprising a nitroimidazole anti-infective residue covalently attached via a stable or degradable linkage to a water-soluble, non-peptidic oligomer, wherein the nitroimidazole anti-infective has a structure encompassed by the following formula:

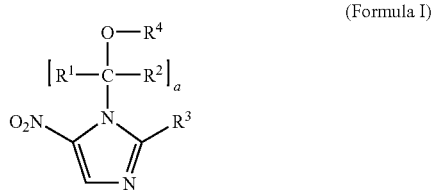

(Formula I)

wherein:

(a) is 2, 3, or 4;

each instance of $R^1$ is independently selected from the group consisting of hydrogen and alkyl (preferably hydrogen);

each instance of $R^2$ is independently selected from the group consisting of hydrogen and alkyl (preferably hydrogen);

$R^3$ is selected from the group consisting of hydrogen and alkyl (preferably $C_{1-5}$ alkyl); and $R^4$ is selected from the group consisting of hydrogen, alkyl, acyl residue of a monocarboxylic aliphatic acid, acyl residue of a dicarboxylic aliphatic acid, acyl residue of a monocarboxylic aromatic acid and acyl residue of a dicarboxylic aromatic acid.

Examples of specific nitroimidazole anti-infectives include those selected from the group consisting of 1-(2-hydroxyethyl)-2-methyl-5-nitroimidazole; 1-(3-hydroxypropyl)-2-methyl-5-nitroimidazole; 1-(2-hydroxyethyl)-2-ethyl-5-nitroimidazole; 1-(2-dichloroacetoxyethyl)-2-methyl-5-nitroimidazole; 1-(2-acetoxyethyl)-2-methyl-5-nitroimidazole; 1-(2-stearoyloxyethyl)-2-methyl-5-nitroimidazole; 1-(2-cinnamoyloxyethyl)-2-methyl-5-nitroimidazole; 1-(2-salicyloyloxyethyl)-2-methyl-5-nitroimidazole; 1-(2-benzoyloxyethyl)-2-methyl-5-nitroimidazole; 1-(2-o-chlorobenzoyloxyethyl)-2-methyl-5-nitroimidazole; 1-[2-(3:4:5-trimethoxy-benzoyloxy)ethyl]-2-methyl-5-nitroimidazole; 1-(2-p-methoxy-benzoyloxyethyl)-2-methyl-5-nitroimidazole; 1-(2-o-nitrobenzoyloxyethyl)-2-methyl-5-nitroimidazole; and 1-(2-pivalyloxyethyl)-2-methyl-5-nitroimidazole.

It is believed that an advantage of the compounds of the present invention is their ability to retain some degree of nitroimidazole anti-infective activity while also exhibiting a decrease in crossing intestinal tissues following oral administration to thereby enter the systemic circulation and/or to provide a longer residence time within the intestinal lumen following oral administration. Although not wishing to be bound by theory, it is believed that the nitroimidazole anti-infective residue- and oligomer-containing compounds described herein—in contrast to the corresponding oligomer-free nitroimidazole anti-infective structure—are not able to pass (extracellularly and/or intracellularly) through the intestinal tissues as readily because the additional size introduced by the oligomer serves to reduce the ability to cross through the intestinal issues into the circulator system. Even should the linkage between the residue of the nitroimidazole anti-infective and the oligomer be degradable, the compound still offers advantages, such as increasing the activity (relative to the oligomer-containing compound) of the compound resulting from degradation of the linkage. In such a case, even a compound of the invention with a degradable linkage may still provide for increased time in the intestine.

With respect to intestinal absorption, the water-soluble, non-peptidic oligomer-small molecule drug compound exhibits intestinal absorption that is reduced as compared to the crossing rate of the small molecule drug not attached to the water-soluble, non-peptidic oligomer. Preferred exemplary reductions in intestinal absorption for the compounds described herein include reductions of: at least about 30%; at least about 40%; at least about 50%; at least about 60%; at least about 70%; at least about 80%; or at least about 90%, when compared to the intestinal absorption of the small molecule drug not attached to the water-soluble oligomer. A preferred reduction in the intestinal absorption for a compound of the invention is at least about 20%.

As indicated above, the compounds of the invention include a nitroimidazole anti-infective residue. Assays for determining whether a given compound (regardless of whether the compound includes a water-soluble, non-peptidic oligomer or not) can act as an anti-infective are described infra.

In some instances, nitroimidazole anti-infectives can be obtained from commercial sources. In addition, nitroimidazole anti-infectives can be obtained through chemical synthesis. Examples of nitroimidazole anti-infectives as well as synthetic approaches for preparing nitroimidazole anti-infectives are described in the literature and in, for example, U.S. Pat. No. 2,944,061.

Each of these (and other) nitroimidazole anti-infectives can be covalently attached (either directly or through one or more atoms) to a water-soluble and non-peptidic oligomer.

Exemplary molecular weights of small molecule drugs include molecular weights of: less than about 950 Daltons; less than about 900 Daltons; less than about 850 Daltons; less than about 800 Daltons; less than about 750 Daltons; less than about 700 Daltons; less than about 650 Daltons; less than about 600 Daltons; less than about 550 Daltons; less than about 500 Daltons; less than about 450 Daltons; less than about 400 Daltons; less than about 350 Daltons; and less than about 300 Daltons.

The small molecule drug used in the invention, if chiral, may be in a racemic mixture, or an optically active form, for example, a single optically active enantiomer, or any combination or ratio of enantiomers (i.e., scalemic mixture). In addition, the small molecule drug may possess one or more geometric isomers. With respect to geometric isomers, a composition can comprise a single geometric isomer or a mixture of two or more geometric isomers. A small molecule drug for use in the present invention can be in its customary active form, or may possess some degree of modification. For example, a small molecule drug may have a targeting agent, tag, or transporter attached thereto, prior to or after covalent attachment of an oligomer. Alternatively, the small molecule drug may possess a lipophilic moiety attached thereto, such as a phospholipid (e.g., distearoylphosphatidylethanolamine or "DSPE," dipalmitoylphosphatidylethanolamine or "DPPE,"

and so forth) or a small fatty acid. In some instances, however, it is preferred that the small molecule drug moiety does not include attachment to a lipophilic moiety.

The nitroimidazole anti-infective for coupling to a water-soluble, non-peptidic oligomer possesses a free hydroxyl, carboxyl, thio, amino group, or the like (i.e., "handle") suitable for covalent attachment to the oligomer. In addition, the nitroimidazole anti-infective can be modified by introduction of a reactive group, preferably by conversion of one of its existing functional groups to a functional group suitable for formation of a stable covalent linkage between the oligomer and the drug.

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; α-hydroxy acid, such as lactic acid or glycolic acid; phosphazene, oxazoline, amino acids, carbohydrates such as monosaccharides, saccharide or mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble, non-peptidic oligomer (e.g., "POLY" in various structures provided herein) can have any of a number of different geometries. For example, it can be linear, branched, or forked. Most typically, the water-soluble, non-peptidic oligomer is linear or is branched, for example, having one branch point. Although much of the discussion herein is focused upon poly(ethylene oxide) as an illustrative oligomer, the discussion and structures presented herein can be readily extended to encompass any of the water-soluble and non-peptidic oligomers described above.

The molecular weight of the water-soluble, non-peptidic oligomer, excluding the linker portion, is generally relatively low. Exemplary values of the molecular weight of the water-soluble polymer include: below about 5000 Daltons, below about 2500 Daltons, below about 2000 Daltons, below about 1500 Daltons; below about 1450 Daltons; below about 1400 Daltons; below about 1350 Daltons; below about 1300 Daltons; below about 1250 Daltons; below about 1200 Daltons; below about 1150 Daltons; below about 1100 Daltons; below about 1050 Daltons; below about 1000 Daltons; below about 950 Daltons; below about 900 Daltons; below about 850 Daltons; below about 800 Daltons; below about 750 Daltons; below about 700 Daltons; below about 650 Daltons; below about 600 Daltons; below about 550 Daltons; below about 500 Daltons; below about 450 Daltons; below about 400 Daltons; below about 350 Daltons; below about 300 Daltons; below about 250 Daltons; below about 200 Daltons; and below about 100 Daltons.

Exemplary ranges of molecular weights of the water-soluble, non-peptidic oligomer (excluding the linker) include: from about 100 to about 2500 Daltons; from about 100 to about 2200 Daltons; from about 100 to about 2100 Daltons; from about 200 to about 2100 Daltons; from about 500 to about 2100 Daltons; from about 750 to about 2100 Daltons; from about 1000 to about 2100 Daltons; from about 75 to 1000 Daltons; and from about 75 to about 750 Daltons.

In some instances, the number of monomers in the water-soluble, non-peptidic oligomer falls within one or more of the following ranges: between about between about 1 and about 125 (inclusive); between about 1 and about 55; between about 3 and about 50; between about 10 and about 50; between about 20 and about 50; between about 31 and about 125. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers. In yet further embodiments, the oligomer (and the corresponding conjugate) possesses 21, 22, 23, 24, 25, 26, 27, 28, 29 or 30 monomers in series. In still other embodiments, the oligomer (and the corresponding conjugate) possesses 31, 32, 33, 34, 35, 36, 37, 38, 39 or 40 monomers. It still further embodiments, the oligomer (and the corresponding conjugate) possesses 41, 42, 43, 44, 45, 46, 47, 48, 49 or 50 monomers. Thus, for example, when the water-soluble and non-peptidic polymer includes $CH_3$—$(OCH_2CH_2)_n$—, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: between about 1 and about 25; between about 1 and about 20; between about 1 and about 15; between about 1 and about 12; between about 1 and about 10.

When the water-soluble, non-peptidic oligomer has 1, 2, 3, 4, 5, 6, 7, 8, 9, or 10 monomers, these values correspond to a methoxy end-capped oligo(ethylene oxide) having a molecular weights of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the water-soluble, non-peptidic oligomer is attached to the nitroimidazole anti-infective (in contrast to the stepwise addition of one or more monomers to effectively "grow" the oligomer onto the nitroimidazole anti-infective), it is preferred that the composition containing an activated form of the water-soluble, non-peptidic oligomer be monodisperse. In those instances, however, where a bimodal composition is employed, the composition will possess a bimodal distribution centering around any two of the above numbers of monomers. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth. Relatively polydisperse oligomers (such as those around 2,000 Daltons) can also be used.

In some instances, the composition containing an activated form of the water-soluble, non-peptidic oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

It is preferred that the water-soluble, non-peptidic oligomer is obtained from a composition that is preferably unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble and non-peptidic oligomers can be prepared as described in Chen Y., Baker, G. L., J. Org. Chem., 6870-6873 (1999), WO 02/098949, and U.S. Patent Application Publication 2005/0136031.

When present, the spacer moiety (through which the water-soluble and non-peptidic polymer is attached to the nitroimidazole anti-infective) may be a single bond, a single atom, such as an oxygen atom or a sulfur atom, two atoms, or a number of atoms. A spacer moiety is typically but is not necessarily linear in nature. The spacer moiety, "X," is hydrolytically stable, and is preferably also enzymatically stable. Preferably, the spacer moiety "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—NH—C(O)—NH—). In selected embodiments, the linkage does not comprise further spacer groups.

In some instances, the spacer moiety "X" comprises an ether, amide, urethane, amine, thioether, urea, or a carbon-carbon bond. Functional groups such as those discussed below, and illustrated in the examples, are typically used for forming the linkages. The spacer moiety may less preferably also comprise (or be adjacent to or flanked by) other atoms, as described further below.

More specifically, in selected embodiments, a spacer moiety of the invention, X, may be any of the following: "—" (i.e., a covalent bond, that may be stable or degradable, between the nitroimidazole anti-infective residue and the water-soluble, non-peptidic oligomer), —C(O)O—, —OC(O)—, —CH$_2$—C(O)O—, —CH$_2$—OC(O)—, —C(O)O—CH$_2$—, —OC(O)—CH$_2$—, —O—, —NH—, —S—, —O—C(O)—O—, —CH$_2$—O—C(O)—O—, —O—C(O)—O—CH$_2$—, —C(O)—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—CH$_2$—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl.

For purposes of the present invention, however, a group of atoms is not considered a linkage when it is immediately adjacent to an oligomer segment, and the group of atoms is the same as a monomer of the oligomer such that the group would represent a mere extension of the oligomer chain.

The linkage "X" between the water-soluble, non-peptidic oligomer and the small molecule is typically formed by reaction of a functional group on a terminus of the oligomer (or nascent oligomer when it is desired to "grow" the oligomer onto the nitroimidazole anti-infective) with a corresponding functional group within the nitroimidazole anti-infective. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g. succinimidyl or benzotriazyl carbonate) on the drug, or vice versa, forms a carbamate linkage. Reaction of an amine on an oligomer with an isocyanate (R—N=C=O) on a drug, or vice versa, forms a urea linkage (R—NH—(C=O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde function is coupled to an oligomer amino group by reductive amination, resulting in formation of a secondary amine linkage between the oligomer and the small molecule.

A particularly preferred water-soluble, non-peptidic oligomer is an oligomer bearing an aldehyde functional group. In this regard, the oligomer will have the following structure: CH$_3$O—(CH$_2$—CH$_2$—O)$_n$—(CH$_2$)$_p$—C(O)H, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4. In addition, the carbon atom alpha to the —C(O)H moiety can optionally be substituted with alkyl.

Typically, all but one termini of the water-soluble, non-peptidic oligomer not bearing a functional group is capped to render it unreactive. When the oligomer includes a further functional group at a terminus other than that intended for formation of a conjugate, that group is either selected such that it is unreactive under the conditions of formation of the linkage "X," or it is protected during the formation of the linkage "X."

As stated above, the water-soluble, non-peptidic oligomer includes at least one functional group prior to conjugation. The functional group typically comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine ($-NHNH_2$), hydrazide ($-C(O)NHNH_2$), and thiol. Preferred nucleophiles include amine, hydrazine, hydrazide, and thiol, particularly amine. Most small molecule drugs for covalent attachment to an oligomer will possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and haloslane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate(2,2,2-trifluoroethanesulfonate).

Also included are sulfur analogs of several of these groups, such as thione, thione hydrate, thioketal, is 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

An "activated derivative" of a carboxylic acid refers to a carboxylic acid derivative that reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form $-(CO)O-N[(CO)-]_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form $-(CH_2)_{2-3}C(=O)O-Q$, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g., hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, react with amino groups to form carbamates. Isocyanates (R—N=C=O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e., aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, can be added, to form, for example, thioether bonds. These groups include maleimides, vinyl sulfones, vinyl pyridine, acrylates, methacrylates, and acrylamides. Other groups comprise leaving groups that can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the nitroimidazole anti-infective may not have a functional group suited for conjugation. In this instance, it is possible to modify (or "functionalize") the "original" nitroimidazole anti-infective so that it does have a functional group suited for conjugation. For example, if the nitroimidazole anti-infective has an amide group, but an amine group is desired, it is possible to modify the amide group to an amine group by way of a Hofmann rearrangement, Curtius rearrangement (once the amide is converted to an azide) or Lossen rearrangement (once amide is concerted to hydroxamide followed by treatment with tolyene-2-sulfonyl chloride/base).

It is possible to prepare a conjugate of small molecule nitroimidazole anti-infective bearing a carboxyl group wherein the carboxyl group-bearing small molecule nitroimidazole anti-infective is coupled to an amino-terminated oligomeric ethylene glycol, to provide a conjugate having an amide group covalently linking the small molecule nitroimidazole anti-infective to the oligomer. This can be performed, for example, by combining the carboxyl group-bearing small molecule nitroimidazole anti-infective with the amino-terminated oligomeric ethylene glycol in the presence of a coupling reagent, (such as dicyclohexylcarbodiimide or "DCC") in an anhydrous organic solvent.

Further, it is possible to prepare a conjugate of a small molecule nitroimidazole anti-infective bearing a hydroxyl group wherein the hydroxyl group-bearing small molecule nitroimidazole anti-infective is coupled to an oligomeric ethylene glycol halide to result in an ether (—O—) linked small molecule conjugate. This can be performed, for example, by using sodium hydride to deprotonate the hydroxyl group followed by reaction with a halide-terminated oligomeric ethylene glycol.

Further, it is possible to prepare a conjugate of a small molecule nitroimidazole anti-infective bearing a hydroxyl group wherein the hydroxyl group-bearing small molecule nitroimidazole anti-infective is coupled to an oligomeric ethylene glycol bearing an haloformate group [e.g., $CH_3$($OCH_2CH_2OC(O)$-halo, where halo is chloro, bromo, iodo] to result in an carbonate [—O—C(O)—O—] linked small molecule conjugate. This can be performed, for example, by combining a small molecule nitroimidazole anti-infective and an oligomeric ethylene glycol bearing an haloformate group in the presence of a nucleophilic catalyst (such as 4-dimethylaminopyridine or "DMAP") to thereby result in the corresponding carbonate-linked conjugate.

In another example, it is possible to prepare a conjugate of a small molecule nitroimidazole anti-infective bearing a ketone group by first reducing the ketone group to form the corresponding hydroxyl group. Thereafter, the small molecule nitroimidazole anti-infective now bearing a hydroxyl group can be coupled as described herein.

In still another instance, it is possible to prepare a conjugate of a small molecule nitroimidazole anti-infective bearing an amine group. In one approach, the amine group-bearing small molecule nitroimidazole anti-infective and an aldehyde-bearing oligomer are dissolved in a suitable buffer after which a suitable reducing agent (e.g., NaCNBH$_3$) is added. Following reduction, the result is an amine linkage formed between the amine group of the amine group-containing small molecule nitroimidazole anti-infective and the carbonyl carbon of the aldehyde-bearing oligomer.

In another approach for preparing a conjugate of a small molecule nitroimidazole anti-infective bearing an amine group, a carboxylic acid-bearing oligomer and the amine group-bearing small molecule nitroimidazole anti-infective are combined, typically in the presence of a coupling reagent (e.g., DCC). The result is an amide linkage formed between the amine group of the amine group-containing small molecule nitroimidazole anti-infective and the carbonyl of the carboxylic acid-bearing oligomer.

Exemplary conjugates of the nitroimidazole anti-infectives of Formula I include those having the following structure:

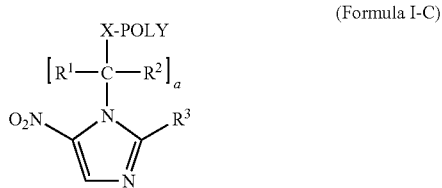

(Formula I-C)

wherein:
each instance of R$^1$ is independently selected from the group consisting of hydrogen and alkyl (preferably hydrogen);
each instance of R$^2$ is independently selected from the group consisting of hydrogen and alkyl (preferably hydrogen);
R$^3$ is selected from the group consisting of hydrogen and alkyl (preferably C$_{1-5}$ alkyl);
X is a spacer moiety; and
POLY is a water-soluble, non-peptidic oligomer.

One of ordinary skill in the art, using routine experimentation, can determine a suitable molecular size and linkage for the conjugates of the invention by first preparing a series of oligomers with different weights and functional groups, forming conjugates therefrom, and then testing the conjugates for the desired activity.

Animal models (rodents and dogs) can be used to study oral drug transport. In addition, non-in vivo methods include rodent everted gut excised tissue and Caco-2 cell monolayer tissue-culture models. These models are useful in predicting oral drug bioavailability. In some instances, it is preferred that the oral bioavailability of the oligomer-containing species is lower than the oral bioavailability of metronidazole.

To determine whether the nitroimidazole anti-infective or the conjugate of a nitroimidazole anti-infective and a water-soluble non-peptidic polymer has activity as an anti-infective, it is possible to test such a compound. For example, a compound of interest can be tested for activity against *Giardia intestinalis* (synonymous with *Giardia lamblia* and *Giardia duodenalis*. Briefly, a compound can be tested at six different concentrations with a three-fold dilution between each concentration (i.e., 10, 3.3, 1.1, 0.37, 0.122, 0.04 μg/ml). Each compound assay can be tested against a *Giardia intestinalis* isolate (such as the WB-1b, BRIS/87/HEPU/713 or BRIS/83/HEPU/106 lines) by individually contacting a composition of the compound of interest with a separate preparation of the isolate. After a period of time, e.g., 24-48 hours, inspection of the isolate for inhibition or growth (or a decrease in colony number) reveals anti-infective activity. Other approaches for testing anti-infective activity are described in, for example, Uperoft et al. (1999) *Antimicrob. Agents Chemother.* 43(1): 73-76 and Uperoft et al. (2006) *Antimicrob. Agents Chemother.* 50(1):344-347.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, excipients will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients and general teachings regarding pharmaceutical compositions are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, flow agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The conjugate can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The conjugate can also be formulated into a suppository for rectal administration. With respect to suppositories, the conjugate is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering a conjugate as provided herein to a patient suffering from a condition that is responsive to treatment with the conjugate. The method comprises administering, generally orally, a therapeutically effective amount of the conjugate (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

The method of administering may be used to treat any condition that can be remedied or prevented by administration of the particular conjugate. For example, it is believed that the conjugate can be used to treat a patient suffering from *Trichomonas vaginalis* infections, *Giardia duodenalis* (synonymous with *Giardia lamblia* and *Giardia intestinalis*) infections, anaerobic infections (e.g., infections caused by *Bacteroides fragilis*), intra-abdominal infections [e.g., peritonitis, intra-abdominal abscesses and liver abscesses cased by *Bacteroides* species (such as *Bacteroides fragilis, Bacteroides distasonis, Bacteroides ovatus, Bacteroides thetaiotamicron* and *Bacteroides vulgatus*), *Clostridium* species, *Eubacterium* species, *Peptostreptococcus* species and *Peptococcus niger*], skin and skin structure infections (e.g., infections caused by *Bacteroides* species, including the *Bacteroides fragilis* group, *Clostridium* species, *Peptococcus niger, Peptostreptococcus* species and *Fusobacterium* species), gynecologic infections (e.g., endometritis, endomyometritis, tubo-ovarian abscesses, and postsurgical vaginal cuff infection caused by *Bacteroides* species, including the *Bacteroides fragilis* group, *Clostridium* species, *Peptococcus niger*, and *Peptostreptococcus* species, and bacterial vaginosis), bacterial septicemia (e.g., bacterial septicemia caused by *Bacteroides* species including the *Bacteroides fragilis* group and *Clostridium* species), bone and joint infections (e.g., bone and joint infections caused by *Bacteroides* species including the *Bacteroides fragilis* group), CNS infections (e.g., meningitis and brain abscesses caused by *Bacteroides* species including the *Bacteroides fragilis* group), respiratory tract infections (e.g., pneumonia, empyema, and lung abscesses caused by *Bacteroides* species including the *Bacteroides fragilis* group), endocarditis caused by *Bacteroides* species (including the *Bacteroides fragilis* group), amebiasis, trichomoniasis, bacterial vaginosis, acne rosacea, hepatic encephalopathy, Crohn's disease, diarrhea associated with *Clostridium difficile, Heliobacter pylori* infections, recurrent urethritis, and pelvic inflammatory disease. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

All articles, books, patents, patent publications and other publications referenced herein are incorporated by reference in their entireties.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All chemical reagents referred to in the appended examples are commercially available unless otherwise indicated. The preparation of PEG-mers is described in, for example, U.S. Patent Application Publication No. 2005/0136031.

All $^1$H NMR (nuclear magnetic resonance) data was generated by an NMR spectrometer manufactured by Bruker.

EXAMPLES 1-5

Preparation of Oligomer-Containing Compounds

Oligomer-containing compounds were prepared in accordance with the schematic provided below.

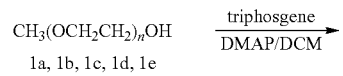

where n = 3 in 1a; n = 7 in 1b; n = 11 in 1c; n = 21 in 1d; and n = a number so as to provide a polyethylene oxide of about 1kDa in 1e

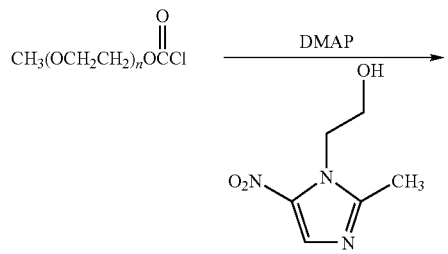

-continued

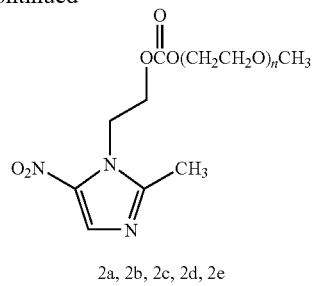

2a, 2b, 2c, 2d, 2e where n = 3 in 2a; n = 7 in 2b;
n = 11 in 2c; n = 21 in 2d; and
n = a number so as to provide a
polyethylene oxide of about 1kDa
in 2e

Example 1

Preparation of mPEG$_3$ Metronidazole Carbonate (2a)

mPEG$_3$OH (1.0 mmol, 164 mg) and DMAP [4-(dimethylamino)pyridine, 2.4 mmol] were dissolved in anhydrous DCM (dichloromethane, 20 ml). Triphosgene (0.34 mmol, 99 mg) was added at room temperature. The solution was stirred at room temperature for 15 minutes. Metronidazole (1.0 mmol, 171 mg) was added and the reaction solution was stirred at room temperature for two hours. The solvent was evaporated at reduced pressure. The residue was subjected to flash chromatography (methanol/DCM=2~5%) to obtain compound 2a (220 mg, yield 61%). $^1$H NMR (CDCl$_3$) δ 7.99 (s, 1H), 4.61 (t, 2H), 4.50 (t, 2H), 4.28 (t, 2H), 3.73-3.40 (m, 10H), 3.40 (s, 3H), 2.53 (s, 3H). LC/MS 362 [M+H]$^+$.

Example 2

Preparation of mPEG$_7$ Metronidazole Carbonate (2b)

mPEG$_7$OH (1.0 mmol, 340 mg) and DMAP (2.4 mmol) were dissolved in anhydrous DCM (20 ml). Triphosgene (0.34 mmol, 99 mg) was added at room temperature. The solution was stirred at room temperature for 15 minutes. Metronidazole (1.0 mmol, 171 mg) was added and the reaction solution was stirred at room temperature for two hours. The solvent was evaporated at reduced pressure. The residue was subjected to flash chromatography (methanol/DCM=2~5%) to obtain compound 3a (212 mg, yield 39%). $^1$H NMR (CDCl$_3$) δ 7.28 (s, 1H), 4.60 (t, 2H), 4.51 (t, 2H), 4.27 (t, 2H), 3.72-3.40 (m, 26H), 3.39 (s, 3H), 2.53 (s, 3H). LC/MS 538 [M+H]$^+$.

Example 3

Preparation of mPEG$_{11}$ Metronidazole Carbonate (2c)

mPEG$_{11}$OH (0.39 mmol, 200 mg) and DMAP (0.93 mmol) were dissolved in anhydrous DCM (10 ml). Triphosgene (0.13 mmol, 38.5 mg) was added at room temperature. The solution was stirred at room temperature for ten minutes. Metronidazole (0.43 mmol, 73.5 mg) was added and the reaction solution was stirred at room temperature overnight. The solvent was evaporated at reduced pressure. The residue was subjected to flash chromatography (methanol/DCM=2~5%) to obtain compound 2c (107 mg, yield 38%). $^1$H NMR (CDCl$_3$) δ 7.92 (s, 1H), 4.55 (t, 2H), 4.45 (t, 2H), 4.21 (t, 2H), 3.66-3.49 (m, 42H), 3.33 (s, 3H), 2.47 (s, 3H). LC/MS 714 [M+H]$^+$.

Example 4

Preparation of mPEG$_{21}$ Metronidazole Carbonate (2d)

mPEG$_{21}$OH (0.21 mmol, 200 mg) and DMAP (1.0 mmol) were dissolved in anhydrous DCM (10 ml). Triphosgene (0.13 mmol, 39 mg) was added at room temperature. The solution was stirred at room temperature for 5 minutes. Metronidazole (1.0 mmol, 171 mg) was added and the reaction solution was stirred at room temperature overnight. The solvent was evaporated at reduced pressure. The residue was extracted with EtOAc/H$_2$O (20 ml/20 ml) three times. The aqueous phases were combined and adjusted to PH 4.0 by adding 0.1N HCl solution. The solution was extracted with DCM (3×20 ml). The organic phases were combined and dried with anhydrous Na$_2$SO$_4$. The solid was filtered off and the solvent was evaporated to give compound 2d (220 mg, yield 90%). $^1$H NMR (CDCl$_3$) δ 7.89 (s, 1H), 4.53 (t, 2H), 4.43 (t, 2H), 4.19 (t, 2H), 3.63-3.46 (m, 80H), 3.31 (s, 3H), 2.45 (s, 3H). LC/MS 1154 [M+H]$^+$.

Example 5

Preparation of mPEG1k Metronidazole Carbonate (2e)

mPEG$_{1\,kDa}$OH (1.0 mmol, 1.0 g) and DMAP (2.4 mmol) were dissolved in anhydrous DCM (20 ml). Triphosgene (0.33 mmol, 99 mg) was added at room temperature. The solution was stirred at room temperature for 15 minutes. Metronidazole (1.1 mmol, 188 mg) was added and the reaction solution was stirred at room temperature for four hours. The solvent was evaporated at reduced pressure. The residue was extracted with DCM and 1N HCl solution (20 ml/20 ml) twice. The organic phases were combined and dried with anhydrous Na$_2$SO$_4$. The solid was filtered off and the solvent was evaporated. The residue was precipitated in ethyl ether/IPA (20 ml/10 ml). The compound 2e (590 mg, yield 50%) as solid was obtained by filtration. $^1$H NMR (CDCl$_3$) δ 7.98 (s, 1H), 4.60 (t, 2H), 4.50 (t, 2H), 4.27 (t, 2H), 3.74-3.54 (m, 96H), 3.39 (s, 3H), 2.52 (s, 3H). MW 1308 [M+H]$^+$.

Example 6

In Vitro Antigiardial Activity of Compounds Against *Giardia Intestinalis*

Metronidazole (from two different sources) and samples prepared in accordance with Examples 1 and 2 were tested using conventional antimicrobial assay techniques for in vitro antigiardial activity at six concentrations with three-fold dilutions (10, 3.3, 1.1, 0.37, 0.122, 0.04 µg/mL). IC$_{50}$ values (inhibition concentration) were determined. Results are provided in Table 1.

TABLE 1

In Vitro Antigiardial Activity Assay

| Compound | µg/ml | | | | | | | µM |
| | $IC_{50}$ 1 | $IC_{50}$ 2 | $IC_{50}$ 3 | Average $IC_{50}$ | AVEDEV | STDEV | MW | $IC_{50}$ |
|---|---|---|---|---|---|---|---|---|
| Metronidazole | 0.75 | 0.58 | 0.7 | 0.68 | 0.064 | 0.087 | 171 | 3.96 |
| $PEG_3$ Metronidazole carbonate | 0.82 | 1.1 | 1.2 | 1.04 | 0.147 | 0.197 | 361 | 2.88 |
| $PEG_7$ Metronidazole carbonate | 4.5 | 4.2 | 3.4 | 4.03 | 0.422 | 0.569 | 537 | 7.51 |
| Metronidazole (Sigma Chem) | 0.75 | 0.3 | 0.7 | 0.58 | 0.189 | 0.247 | 171 | 3.41 |

Example 7

Minimum Inhibitory Concentration Determinations

The minimum inhibitory concentration (MIC) for metronidazole and the samples prepared in accordance with Examples 1, 3, 4 and 5 were assayed. Although the MIC for the sample prepared in accordance with Example 2 was also assayed, correct execution of the assay could not be confirmed; as a consequence, the data for that sample raised questions of validity and are not included.

Briefly, minimum inhibitory concentration was evaluated in an anti-protozoal assay against a protozoan strain, *Giardia intestinalis* Portland-1 (ATCC 30888), isolated from human. The organism, also referred to as *Giardia lamblia*, causes infection in the small intestine.

The susceptibility of *G. intestinalis* to the test compounds was determined using the micro-broth dilution analysis. The protozoan strain was cultured according to the supplier's recommendations. Thirteen milliliters of growth media (TYI-S-33 supplemented with bile) was inoculated with 100 µL, of *G. intestinalis* growing culture and incubated at 37° C. for 72 hours. Following incubation, each test compound was diluted (in growth medium) to two times the high test concentration then further diluted in 1:2 increments to yield 11 test concentrations. Each test concentration (100 µL) was added in triplicate to designated wells on the plate. Trophozoites were added to each well of a 96-well round bottom plate in a volume of 100 µL at a density of 40,000 per well. The plates were cultured for 24 hours in an anaerobic chamber to assure the presence of low oxygen level.

Following the treatment incubation, cultures were visually evaluated for trophozoite motility. At each concentration, data was recorded as positive or negative for motility. The lowest concentration of the test compound that completely inhibited trophozoite motility was considered the MIC.

Each test compound was dissolved in DMSO to a final concentration of 80 mM. No effect on motility of the organism was seen with the DMSO (solvent control). The starting high test concentration was to be as high as possible. The MIC of the compounds ranged between 3.9 and >1000 µg/mL. Results are provided in Table 2.

TABLE 2

Minimum Inhibitory Concentration Determinations in *Giardia intestinalis* (Human)

| Compound | High Test Concentration (µg/mL) | Test Concentrations (µg/mL) | MIC (µg/mL) | Fold Difference (Parent vs. Derivative) |
|---|---|---|---|---|
| Metronidazole | 250 | 0, 0.24, 0.49, 0.98, 1.95, 3.9, 7.8, 15.6, 31.25, 62.5, 125, 250 | 3.9 | 1 |
| $mPEG_3$ metronidazole carbonate (Example 1) | 500 | 0, 0.49, 0.98, 1.95, 3.9, 7.8, 15.6, 31.25, 62.5, 125, 250, 500 | 7.8 | 2 |
| $mPEG_{11}$ metronidazole carbonate (Example 3) | 1000 | 0, 0.98, 1.95, 3.9, 7.8, 15.6, 31.25, 62.5, 125, 250, 500, 1000 | 1000 | 256 |
| $mPEG_{21}$ metronidazole carbonate (Example 4) | 1000 | 0, 0.98, 1.95, 3.9, 7.8, 15.6, 31.25, 62.5, 125, 250, 500, 1000 | 1000 | 256 |
| mPEG1K metronidazole carbonate (Example 5) | 1000 | 0, 0.98, 1.95, 3.9, 7.8, 15.6, 31.25, 62.5, 125, 250, 500, 1000 | >1000 | >256 |

*Giardia intestinalis* was most sensitive to the parent compound, metronidazole, at 3.9 µg/mL. The next most active compound, $mPEG_3$ metronidazole carbonate had an MIC of 7.8. Although reductions of activity were seen for the PEG $PEG_{11}$, $PEG_{21}$ and PEG1k conjugates, dosage adjustments in vivo and/or use of a degradable linkage may address these reductions.

What is claimed is:

1. A compound of the structure:

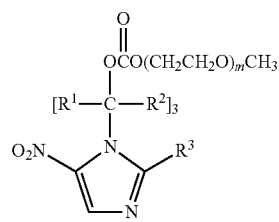

wherein:
(a) is 2 or 3;
each instance of $R^1$ is hydrogen;
each instance of $R^2$ is hydrogen;

$R^3$ is selected from the group consisting of hydrogen, methyl and ethyl; and (n) is an integer of from 3 to 7 inclusive.

2. The compound of claim 1, wherein (a) is 2 and $R^3$ is selected from the group consisting of methyl and ethyl.

3. The compound of claim 1, wherein (a) is 2 and $R^3$ methyl.

4. A composition comprising a compound of claim 1 and a pharmaceutically acceptable excipient.

5. A composition of matter comprising a compound of claim 1, wherein the compound is present in a dosage form.

* * * * *